(12) United States Patent
Naddaka et al.

(10) Patent No.: US 6,649,796 B2
(45) Date of Patent: Nov. 18, 2003

(54) PROCESS FOR THE PREPARATION OF ACETAMIDE DERIVATIVES

(75) Inventors: Vladimir Naddaka, Lod (IL); Naim Menashe, Herzliya (IL); Jael Lexner, Tel Aviv (IL); Shadi Saeed, Haifa (IL); Joseph Kaspi, Givatayim (IL); Ori Lerman, Givatayim (IL)

(73) Assignee: Chemagis, Ltd., Tel Aviv (IL)

( * ) Notice: Subject to any disclaimer, the term of this patent is extended or adjusted under 35 U.S.C. 154(b) by 0 days.

(21) Appl. No.: 10/112,776

(22) Filed: Apr. 2, 2002

(65) Prior Publication Data
US 2002/0183552 A1 Dec. 5, 2002

(30) Foreign Application Priority Data
May 13, 2001 (IL) ................................................ 143106

(51) Int. Cl.$^7$ ............................................. C07C 323/29
(52) U.S. Cl. ........................ 564/162; 564/19; 564/124; 564/222
(58) Field of Search ........................ 564/162, 19, 124, 564/222

(56) References Cited

U.S. PATENT DOCUMENTS 4,177,290 A    12/1979    Lafon

FOREIGN PATENT DOCUMENTS

FR    2528038    * 12/1983

* cited by examiner

Primary Examiner—Shailendra Kumar
(74) Attorney, Agent, or Firm—Banner & Witcoff, Ltd.

(57) ABSTRACT

The invention provides a process for the preparation of diphenylmethylthioacetamide (I) as described in Scheme 4 comprising reacting of the isothiouronium salt or its corresponding base of the formula IV with an acetamide of the formula $XCH_2CONH_2$, wherein X represents a halogen, M represents an alkali metal and A represents an anion, in a protic medium at a temperature of less than 100° C.

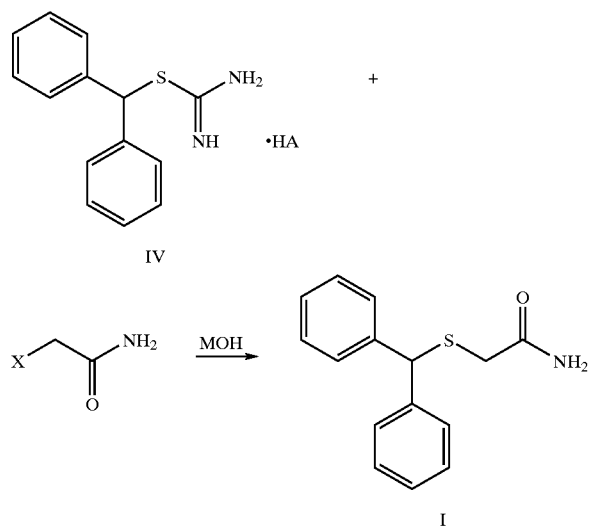

Scheme 4

5 Claims, No Drawings

PROCESS FOR THE PREPARATION OF ACETAMIDE DERIVATIVES

This application claims the benefit of and incorporates by reference co-pending Israeli application No. 143,106 filed May 13, 2001.

The present invention relates to an improved process for the preparation of diphenylmethylthioacetamide (I), a key intermediate in the synthetic pathway for Modafinil.

Modafinil is defined as a CNS stimulant and is marketed under the trade name "Provigil", for the treatment of narcolepsia.

Modafinil was introduced by Lafon. Its preparation, use and pharmacological properties were described in U.S. Pat. No. 4,177,290.

PRIOR ART

U.S. Pat. No. 4,177,290 describes the synthetic pathways for the preparation of Modafinil (III). Both of the pathways described therein use diphenylmethylthioacetic acid (II) as starting material.

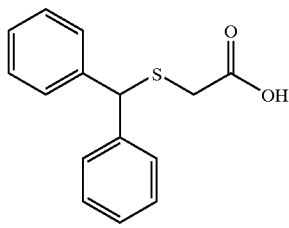

II

One synthetic method is based on the reaction of diphenylmethylthioacetyl chloride (obtained from II and thionyl chloride) with ammonia, followed by oxidizing the thioamide formed with hydrogen peroxide. Total yield, as reported, is 63%

(Scheme I).

Scheme 1

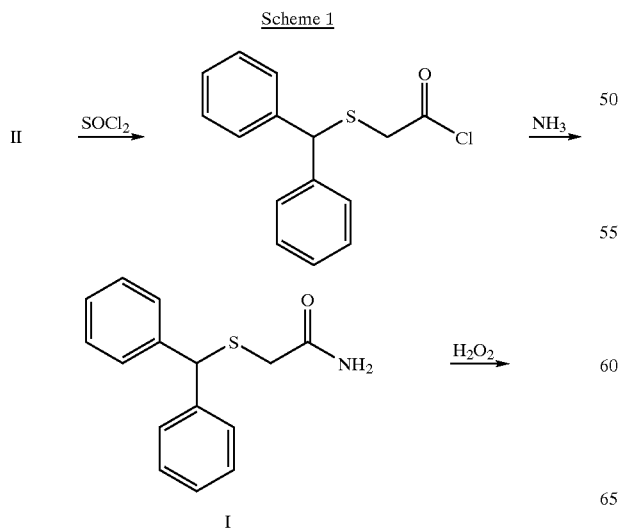

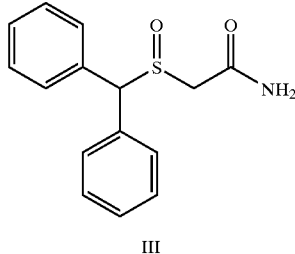

III

A different synthetic pathway described in the same patent involves the oxidation of II as first stage, followed by esterification with dimethylsulfate and amidation with gaseous ammonia. The total yield is 41% (Scheme 2).

Scheme 2

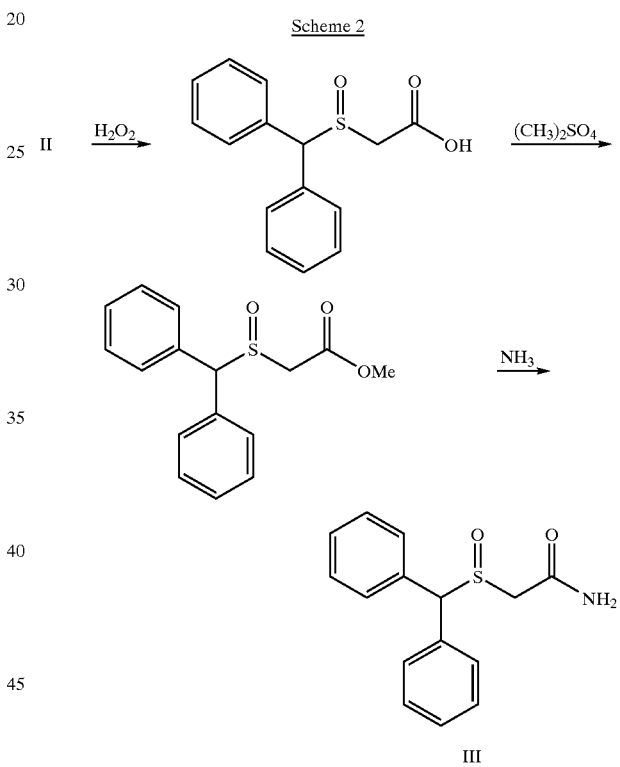

III

Compound II is prepared by the reaction of diphenylmethanol with thiourea in the presence of HBr followed by basic hydrolysis and reaction with chloroacetic acid (Scheme 3).

Scheme 3

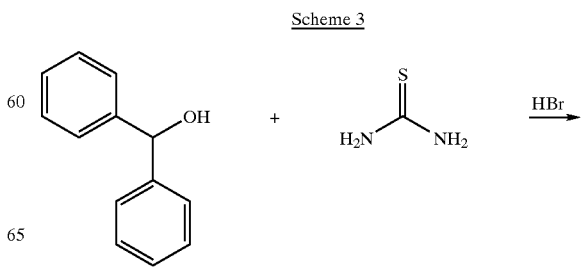

-continued

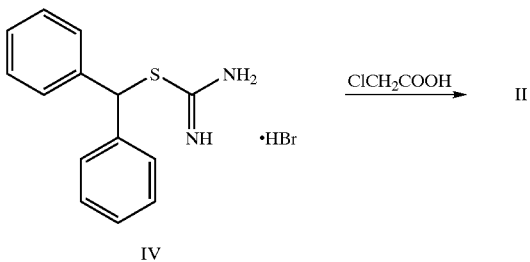

Both synthetic methods involve four chemical steps (starting from diphenylmethanol) and the yields, as reported, are moderate.

Furthermore, both pathways involve toxic and dangerous reagents such as dimethylsulfate, ammonia and thionyl chloride.

In order to improve the synthetic method, according to the present invention there is now reacted the isothiouronium salt (IV) (obtained from the reaction between diphenylmethanol and thiourea) with haloacetamide.

According to the present invention it has now been found that haloacetamide reacts with the isothiouronium salt (IV) in protic solvents (like alcohols or water) at temperatures ranging from 0–100° C. in the presence of a strong base, such as alkali metal hydroxide.

Preferably, chloracetamide is reacted with the said isothiouronium salt in water at 60–70° C. using sodium hydroxide as base.

When the reaction is carried out under the above-mentioned conditions diphenylmethylthioacetamide is obtained in 95% yield from diphenylmethanol. Thus according to the present invention there is now provided a process for the preparation of diphenylmethylthioacetamide (I) as described in Scheme 4 comprising reacting of the isothiouronium salt or its corresponding base of the formula IV with an acetamide of the formula $XCH_2CONH_2$, wherein X represents a halogen, M represents an alkali metal and A represents an anion, in a protic medium at a temperature of less than 100° C.

Scheme 4

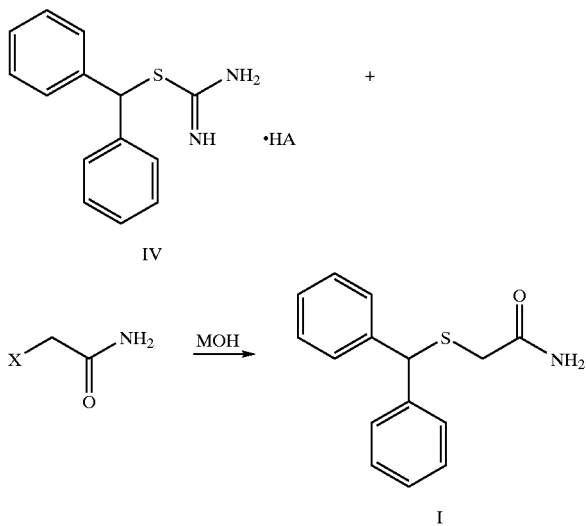

The said method comprises only three chemical steps. It does not involve toxic or corrosive reagents. Very pure Modafinil is obtained at the end of the synthetic pathway at 67% yield (starting from diphenylmethanol).

Thus, diphenylmethanol is reacted with thiourea in the presence of hydrobromic acid in aqueous medium under reflux and then cooled. The isothiouronium salt (IV) formed is filtered and reacted with chloroacetamide under aqueous base conditions at 60–70° C. The solution is cooled and the diphenylmethylthioacetamide formed is filtered and collected.

All the physical properties and the NMR and IR spectra are in perfect agreement with the proposed structure.

The following examples will serve as further illustration and clarification of the present invention.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

REFERENCE EXAMPLE 1

Preparation of Isothiouronium Salt (IV).

Diphenylmethanol (130 g, 0.7 mole) and thiourea (65 g, 0.85 mole) are added in 0.5 l reactor charging with water (325 ml). The mixture is heated to 95° C. (an emulsion is obtained) and 48% HBr 260 gr. 3.22 mole, 4.6 equivalents) is then added gradually during 0.5 hour. The mixture is heated under reflux (106–107° C.) for 0.5 hour and cooled to 80–85° C. At this temperature, the mixture is seeded with several crystals of the product and the mixture is stirred at that temperature for 0.5 hour and then cooled to 250. The colorless crystals are collected by filtration, washed with water (200 ml) yielding about 240 gr. of wet crude isothiouronium salt.

Preparations of Diphenylmethylthioacetamide.

EXAMPLE 1a

A 2 L reactor was charged with diphenylmethylisothiouronium bromide crude wet obtained in reference example 1 (240 gr.) and water (700 ml.) under nitrogen. The suspension was heated to 60° C. and 46% aqueous NaOH solution (98 ml, 1.68 mole, 2.4 eq.) was added. The reaction mixture was heated to 85° C. and stirred until all the solid was dissolved. Then, it was cooled to 60° C. and chloroacetamide (80 g, 0.84 mole, 1.2 eq.) was added in five portions hour at 60–70° C. during one hour. The suspension is stirred at 70° C. for 4–5 hours. The mixture was filtered while warm and the cake was washed with hot water (250 ml). Diphenylmethylthioacetamide crude wet is obtained [220 gr., HPLC assay: 78%, HPLC purity: 95%, yield: 95% (from diphenylmethanol.)]

20 gr. of the product was recrystallized twice from ethyl acetate, dried in vacuo to give 15 gr. of pure title compound.

$^1$H-NMR (CDCl$_3$); δ(ppm)=3.3 (2H, s, CH$_2$), 5.18 (1H, s, CH), 6.54 (2H, bs, NH$_2$), 7.18–7.43 (10H, m, 2× Ph).

$^{13}$C-NMR (CDCl$_3$); δ(ppm)=35.55 (CH$_2$), 54.56 (CH), 127.60, 128.26, 140.20 (Ph), 171.82 (C=O).

EXAMPLE 1b

A 0.5 L reactor was charged with diphenylmethylisothiouronium bromide crude wet (61 gr.) and water (163 ml.) under nitrogen. The suspension was heated to 40° C. and 46% aqueous NaOH solution (25 ml.) was added. The reaction mixture was heated to 80° C. and stirred until all the solid was dissolved. Then, it was cooled to 30° C. and chloroacetamide (19.8 g, 0.21 mole, 1.2 eq., purity 98%) was added in four portions during one hour. The suspension was stirred at 30–35° C. for 4–5 hours. Then the mixture was filtered while warm and the cake was washed with water and a mixture of methanol and water (4:1). The product was dried on air to give diphenylmethylthioacetamide crude wet was obtained [78.3 gr., HPLC assay: 88%, HPLC purity: 88%, yield: 88% (from diphenylmethanol.)]

EXAMPLE 1c

A 0.5 L reactor was charged with diphenylmethylisothiouronium bromide crude wet (61 g.) and methanol (163 ml.) under nitrogen. The suspension was heated to 40–50° C. and 46% aqueous NaOH solution (25 ml.) was added. The reaction mixture was heated to 60° C. and stirred for ½ hour. Chloroacetamide (19.8 g, 0.21 mole, 1.2 eq., purity 98%) was added in two portions during 10 minutes. The suspension was stirred at heating under reflux for 3–4 hours. Then water (80 ml.) was added dropwise at 60–65° C. The mixture was cooled to 30° C. and filtered. The cake was washed with a mixture of methanol and water (4:1) and water. Diphenylmethylthioacetamide crude wet was obtained [34.3 g, HPLC assay: 95%, HPLC purity: 99%, yield: 71% (from diphenylmethanol.)]

EXAMPLE 1d

A 0.5 L reactor was charged with diphenylmethylisothiouronium bromide crude wet (38 g.) and water (117 ml.) under nitrogen. The suspension was heated to 40–50° C. and 46% aqueous NaOH solution (16.4 ml.) was added. The reaction mixture was heated to 80° C. until all the solid had been dissolved. Then it was cooled to ca. 60° C. and bromoacetamide (20 g, 0.142 mole, 1.2 eq., purity 98%) was added in five portions during one hour. The suspension was stirred at 70° C. for 4–5 hours. Then it was filtered while warm and the cake washed with hot water. Diphenylmethylthioacetamide crude wet was obtained [32.7 g, HPLC assay: 78%, HPLC purity: 99%, yield: 90% (from diphenylmethanol.)]

REFERENCE EXAMPLE 2

A 1.0 L reactor was charged with diphenylmethylthioacetamide crude wet (220 gr.) obtained from example 1a and glacial acetic acid (610 ml). The mixture was heated to 40° C. and stirred until full dissolution is achieved. 5.8% $H_2O_2$ solution (500 g, 1.2 eq.) was added dropwise during 0.5 hours at 40–450 C. The reaction mixture was stirred at 40–45° C. for 4 hours. Then sodium metabisulfite (18.3 gr.) in 610 ml. water was added in order to quench the unreacted $H_2O_2$ and the suspension was stirred for 0.5 hours. Then the reaction mixture was cooled to 15° C. and filtered. The cake was washed with water (610 ml.) and dried on air to obtain crude wet Modafinil (205 g). Reslurry in refluxing ethyl acetate, followed by recrystallization from methanol:water (4:1) solution afforded pure Modafinil [(125 g, HPLC assay: 99.9%, HPLC purity: 99.9%, yield: 67% (from diphenylmethanol.)]

It will be evident to those skilled in the art that the invention is not limited to the details of the foregoing illustrative examples and that the present invention may be embodied in other specific forms without departing from the essential attributes thereof. It is therefore desired that the present embodiments and examples be considered in all respects as illustrative and not restrictive, reference being made to the appended claims, rather than to the foregoing description and all the changes which come within the meaning and range of equivalency of the claims are therefore intended to be embraced therein.

What is claimed is:

1. A process for the preparation of diphenylmethylthioacetamide (I) as described in Scheme 4 comprising reacting of the isothiouronium salt or its corresponding base of the formula IV with an acetamide of the formula $XCH_2CONH_2$, wherein X represents a halogen, M represents an alkali metal and A represents an anion, in a protic medium at a temperature of less than 100° C.:

Scheme 4

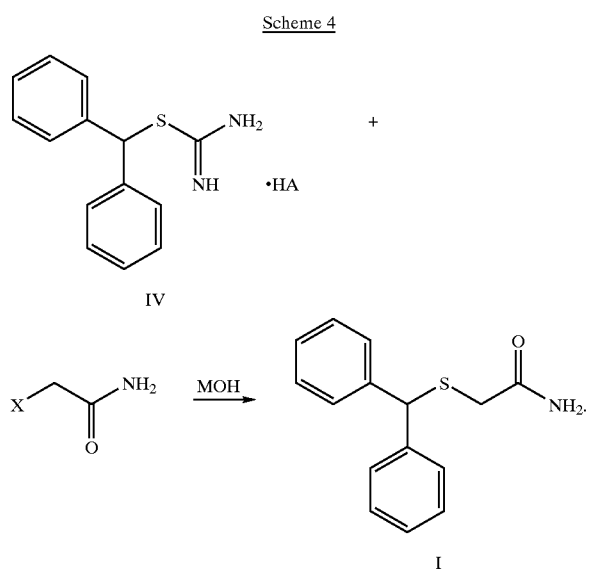

2. A process according to claim 1, wherein X is selected from the group consisting of chlorine and bromine atoms.

3. A process according to claim 1 wherein the reaction takes place at a temperature between 60–70° C.

4. A process according to claim 1 where M is a sodium atom.

5. A process for the preparation of Modafinil (III):

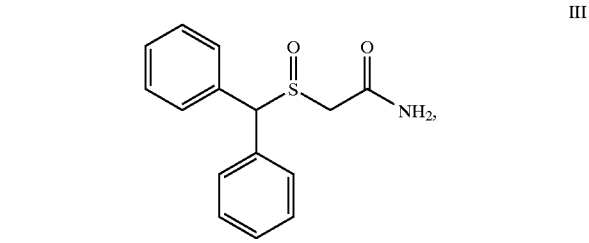

comprising the steps of:

(a) preparing diphenylmethylthioacetamide (I) as described in Scheme 4 comprising reacting of the isothiouronium salt or its corresponding base of the formula IV with an acetamide of the formula XCH₂CONH₂, wherein X represents a halogen, M represents an alkali metal and A represents an anion, in a protic medium at a temperature of less than 100° C.:
Scheme 4
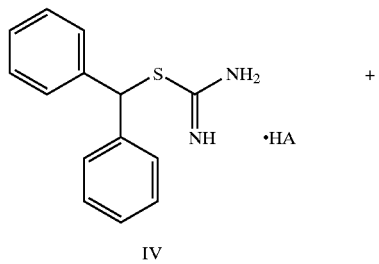
IV
+
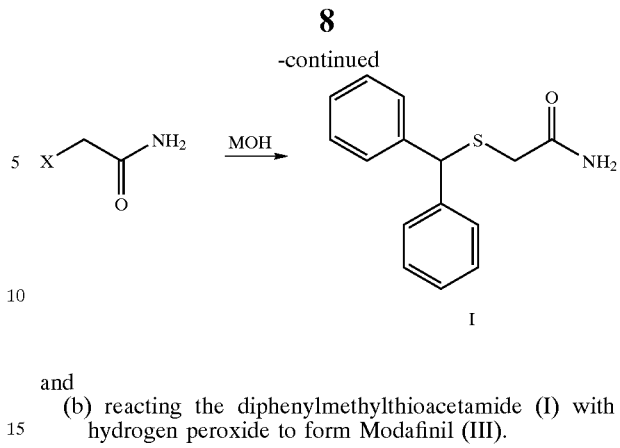
and
(b) reacting the diphenylmethylthioacetamide (I) with hydrogen peroxide to form Modafinil (III).
* * * * *